United States Patent [19]

Panoz et al.

[11] Patent Number: 4,898,737

[45] Date of Patent: Feb. 6, 1990

[54] CONTROLLED ABSORPTION PHARMACEUTICAL COMPOSITION

[75] Inventors: Donald E. Panoz; Edward J. Geoghegan, both of Athlone, Ireland

[73] Assignee: Elan Corporation plc, Athlone, Ireland

[21] Appl. No.: 188,090

[22] Filed: Apr. 27, 1988

Related U.S. Application Data

[63] Continuation of Ser. No. 32,996, Mar. 30, 1987, abandoned, which is a continuation of Ser. No. 598,191, Apr. 9, 1984, abandoned.

[30] Foreign Application Priority Data

Apr. 21, 1983 [IE] Ireland .................................. 915/83

[51] Int. Cl.$^4$ ........................... A61K 9/16; A61K 9/52
[52] U.S. Cl. ......................................... 424/468; 427/3; 424/459; 424/460; 424/473; 424/490; 424/497; 514/965
[58] Field of Search ............... 424/468, 459, 460, 473, 424/490, 497; 427/3; 514/965

[56] References Cited

U.S. PATENT DOCUMENTS

| | | | |
|---|---|---|---|
| 4,138,475 | 2/1979 | McAinsh et al. | 424/459 |
| 4,150,110 | 4/1979 | Yoshida et al. | 424/468 |
| 4,248,856 | 2/1981 | Guley et al. | 424/468 |
| 4,248,857 | 2/1981 | DeNeale et al. | 424/468 |
| 4,248,858 | 2/1981 | Guley et al. | 424/468 |
| 4,309,404 | 1/1982 | DeNeale et al. | 424/468 |
| 4,309,406 | 1/1982 | Guley et al. | 424/468 |

FOREIGN PATENT DOCUMENTS 2039737 8/1980 United Kingdom .

Primary Examiner—Ronald W. Griffin
Attorney, Agent, or Firm—Marla J. Church; Robert H. Falk

[57] ABSTRACT

A sustained absorption propranolol-containing pellet for oral administration comprises a core of propranolol or a pharmaceutically acceptable salt thereof and an organic acid embedded in a polymeric material in a multi-layer arrangement and an outer membrane which permits release of the propranolol at a controlled rate in an aqueous medium. The pellet has a dissolution rate in vitro in an aqueous medium, which when measured in a basket assembly according to U.S. Pharmacopoeia XX at 37° C. and 75 r.p.m., is not more than 15% of the total propranol after 2 hours of measurement in a buffer solution at pH 7.5. Not more than 30% of the total propranolol is released after a total of 4 hours of measurement and not more than 63% of the total propranolol is released after a total of 6 hours.

16 Claims, 2 Drawing Sheets ure of Ser. No. 598,191 filed on Apr. 21, 1983, now abandoned.

CONTROLLED ABSORPTION PHARMACEUTICAL COMPOSITION

This application is a continuation of application Ser. No. 032,996 filed on Mar. 30, 1987, now abandoned, which is a continuation of Ser. No. 598,191 filed on Apr. 21, 1983, now abandoned.

BACKGROUND OF THE INVENTION

1. Field of the Invention

This invention relates to controlled absorption pharmaceutical compositions and, in particular, to a controlled absorption propranolol composition.

2. Description of the Prior Art

Propranolol (1-(isopropylamino)-3-(1-naphthyloxy)-2-propanol is a beta-adrenergic blocking agent and as such is a competitive inhibitor of the effects of catecholamines at beta-adrenergic receptor sites. The principal effect of propranolol is to reduce cardiac activity by diminishing or preventing betaadrenergic stimulation. By reducing the rate and force of contraction of the heart, and decreasing the rate of conduction of impulses through the conducting system, the response of the heart to stress and exercise is reduced. These properties are used in the treatment of angina of effort to reduce the oxygen consumption and increase the exercise tolerance of the heart. Propranolol is also used in the treatment of cardiac arrhythmias to block adrenergic stimulation of cardiac pacemaker potentials. Propranolol is also beneficial in the long term treatment of hypertension. Other uses of propranolol are in the treatment of migraine and anxiety.

Propranolol is normally administered as propranolol hydrochloride tablets. Propranolol hydrochloride tablets are marketed by Imperial Chemical Industries PLC (ICI) under the trade mark Inderal. The normal dosage regimen is 10-40 mg three or four times daily.

A major drawback of oral propranolol therapy is that propranolol is extensively and rapidly metabolised so that only a small proportion of the active ingredient reaches the systemic circulation after oral administration. Propranolol is absorbed from the gastro-intestinal tract with peak plasma concentrations occurring one to two hours after a single dose. It is excreted in the urine as free and conjugated propranolol and as metabolites.

A sustained release form of Inderal for once daily administration is available and is marketed by ICI under the trade mark Inderal LA. This form of propranolol while exhibiting a sustained release of the drug has a relatively poor bioavilability. Furthermore, the absorption varies considerably from individual to individual. Other sustained release forms of propranolol are described in U.S. Pat. Nos. 4,248,857 and 4,248,858.

It is an object of the present invention to provide a controlled absorption form of propranolol which is suitable for once daily administration and which is characterised by a high extent of absorption, which is largely invariable from individual to individual, and hence by a high bioavailability.

DESCRIPTION OF THE PREFERRED EMBODIMENTS

Accordingly, the invention provides a controlled absorption propranolol-containing pellet for oral administration, said pellet comprising a core of propranolol or a pharmaceutically acceptable salt thereof and an organic acid embedded in a polymeric material in a multi-layer arrangement, and an outer membrane which permits release of the propranolol at a controlled rate in an aqueous medium, said pellet having a dissolution rate in a buffer solution at pH 7.5 which when measured in a basket assembly according to U.S. Pharmacopoeia XX at 37° C. and 75 r.p.m., has the following characteristics:

(a) up to 15% of the total propranolol is released during the first two hours of measurement in said assembly;
(b) between 15 and 30% of the total propranolol is released after a total of 4 hours of measurement in said assembly;
(c) between 43 and 63% of the total propranolol is released after a total of 6 hours of measurement in said assembly;
(d) between 75 and 100% of the total propranolol is released after a total of 8 hours of measurement in said assembly; and
(e) between 85 and 100% of the total propranolol is released after a total of 10 hours of measurement in said assembly.

Preferably, the pellet contains propranolol hydrochloride.

Preferably, the organic acid is represented by one or more of the following acids: citric acid, tartaric acid, succinic acid, malic acid, ascorbic acid and fumaric acid.

The propranolol and organic acid are preferably present in a ratio of 2:1.

Preferably, the polymeric material in which the propranolol is embedded has a major proportion of a polymer which is rapidly soluble in water.

The polymeric material may consist solely of a water soluble polymer or, alternatively, it may include a minor proportion of a water insoluble polymer. The ratio of water soluble to water insoluble polymer is determined by the particular combination of polymers selected.

The water soluble polymer is suitably hydroxypropylmethylcellulose, polyvinylpyrrolidone or a polymer sold under the trade mark EUDRAGIT RL. Polymers sold under the Trade Mark EUDRAGIT RL and RS are acrylic resins comprising copolymers of acrylic and methacrylic esters with a low content of quarternary ammonium groups and are described in the "Eudragit" brochure of Rohm Pharma GmbH (1982) wherein detailed physical-chemical data of these products is given. The ammonium groups are present as salts and give rise to permeability of the lacquer films. Eudragit RL and RS are freely permeable (RL) or slightly permeable (RS), respectively independent of pH.

The water insoluble polymer is suitably a cellulose ether such as methyl-, ethyl- or propylcellulose, Shellac or a polymer sold under the trade mark EUDRAGIT RS. Shellac is a resinous excretion of the insect Laccifer (Tachardia) Lacca kerr, order Homoptera, family Coccidae.

The term water-soluble polymer as used herein includes polymers which are freely permeable to water such as Eudragit RL. Likewise the term water-insoluble polymer as used herein includes polymers which are slightly permeable to water such as Eudragit RS.

The core will suitably have between 20 and 120 layers and is built up in a manner known per se.

Further, preferably, the multi-layer arrangement of propranolol, organic acid and polymeric material will be built up on a central inert core suitably consisting of a non-pareil seed having an average diameter in the range 0.3–0.7 mm.

The outer membrane preferably includes a major proportion of a water insoluble polymer.

Further, the outer membrane suitably comprises a major proportion of a water insoluble polymer and a minor proportion of a water soluble polymer, the ratio of water insoluble to water soluble polymer being determined by the inherent solubility characteristics of the polymers selected.

Suitable combinations of water insoluble and water soluble polymers for the rate-controlling membrane include: ethylcellulose and hydroxypropylcellulose in a ratio of 9:1; EUDRAGIT RS AND EUDRAGIT RL in a ratio of 8:2 and Shellac and polyvinylpyrrolidone in a ratio of 9:1.

The outer membrane is formed by applying a number of coats of a solution containing the or each polymer to the core as hereinafter described. Preferably, the number of coats of polymer solution applied is between 30 and 90 coats.

The pellets may be filled into hard gelatin capsules or compressed into tablets using a binder and/or hardening agent commonly employed in tabletting such as microcrystalline cellulose sold under the trademark AVICEL or a co-crystallized powder of highly modified dextrins (3% by weight) and sucrose sold under the trademark DI-PAC.

The invention will be further illustrated by the following Examples.

EXAMPLE 1

Propranolol-containing pellets were prepared in the following manner.

(a) Powder Blend

Propranolol hydrochloride (#100 mesh)(1,000 g), talc (100 g) and citric acid (500 g) were blended in a standard pharmaceutical blender into a uniform powder.

(b) Polymer Solution

A solution of 8 parts (by volume) 10% hydroxypropylmethylcellulose (15 c.p.s.) in methanol/methylene chloride, 60:40 and 2 parts (by volume) 10% ethylcellulose (50 c.p.s.) in methanol/methylene chloride, 60:40 was prepared. Diethylphthalate as a plasticizer was included, as required.

(c) Membrane Solution

The membrane solution was prepared from the following ingredients:

1 part (by volume) 10% hydroxypropylmethylcellulose (15 c.p.s.) in methanol/methylene chloride, 60:40;

9 parts (by volume) 10% ethylcellulose (50 c.p.s.) in methanol/methylene chloride, 60:40;

10 parts (by volume) methanol/methylene chloride, 60:40;

10 parts (by weight) talc;

Diethylphthalate (plasticizer), as required.

Pellet Making Procedure

Step 1.

750 g of starch/sugar seeds (0.4 to 0.5 mm diameter) were placed in a conventional coating pan and rotation was commenced.

Step 2.

The seeds were wetted with sufficient polymer solution (b) to dampen them uniformly.

Step 3.

Powder blend (a) was dusted on until no more adhered to the dampened seeds.

Step 4.

The powder coated seeds were allowed to dry (5–15 minutes).

Steps 2–4 were repeated until all of the powder (a) had been coated on.

Step 5.

The powder coated seeds were sealed with one application of polymer solution (b) and talc.

Step 6.

The powder coated seeds were dried at 45°–50° C. in an oven for at least 12 hours.

Step 7.

The powder coated seeds were placed in a conventional coating pan and rotation was commenced.

Step 8.

A coat of membrane solution (c) was applied to the powder coated seeds and the seeds so coated were allowed to dry. A coat of membrane solution (c) corresponds to 10 ml of solution (c) per 1,000 g of coated seeds.

Step 9.

Two further coats of membrane solution (c) were applied to the coated seeds.

Step 10.

The finished pellets were allowed to dry at 45°–50° C.

The dried pellets were subjected to a dissolution test as follows:

Apparatus:

A Basket Assembly as described in the United States Pharmacopoeia XX at 37° C. and 75 r.p.m.

Buffer:

25 ml of 2.0M potassium chloride and 950 ml of water was adjusted to pH 7.5 with either 0.1N hydrochloric acid or 0.1N sodium hydroxide and the volume made up to 1,000 ml with water.

Sampling Times:

2, 4, 6, 8 and 10 hours.

Method:

2 g of finished pellets were placed in the basket of the assembly and rotation was commenced in 1,000 ml of buffer. At the sampling times, 1.0 ml of the solution was removed and diluted to 50 ml with 0.1N hydrochloric acid. The absorbance of the sample was measured at 290 nm in a spectrophotometer.

The absorbance value equivalent to 100% dissolution was determined by grinding 2 g of pellets in 0.1N hydrochloric acid, filtering, diluting a 1 ml sample to 50 ml with water and measuring the absorbance at 290 nm as before. The percentage dissolution was calculated by division.

Steps 7 to 10 were repeated until the dissolution rate at pH 7.5 was as follows:

| 2 hours | 0–15% |
|---------|-------|
| 4 hours | 15–30% |
| 6 hours | 43–63% |
| 8 hours | 75–100% |
| 10 hours | 85–100% |

A total of 45 coats of membrane solution (c) was applied before the required dissolution rate was obtained.

EXAMPLE 2

Propranolol-containing pellets were prepared in the following manner.

(a) Powder Blend

Propranolol hydrochloride (#100 mesh) (1,000 g), talc (100 g) and ascorbic acid (500 g) were blended in a standard pharmaceutical blender into a uniform powder.

(b) Polymer Solution

A solution of 7 parts (by volume) 5% EUDRAGIT RL in isopropanol/acetone, 60:40 and 3 parts 5% EUDRAGIT RS in isopropanol/acetone, 60:40 was prepared. Diethylphthalate (plasticizer) was included as required.

(c) Membrane Solution

The membrane solution was prepared from the following ingredients:

2 parts (by volume) 5% EUDRAGIT RL in isopropanol/acetone, 60:40;

8 parts (by volume) 5% EUDRAGIT RS in isopropanol/acetone, 60:40;

10 parts (by volume) isopropanol/acetone, 60:40;

10 parts (by weight) talc;

Diethylphthalate (plasticizer), as required.

Pellet Making Procedure

Steps 1–4 were carried out as in Example 1.

Steps 2–4 were repeated until all of the powder (a) had been coated on.

Step 5.

The powder coated seeds were sealed with two applications of polymer solution (b) and talc.

Step 6.

The powder coated seeds were oven dried at 45°–50° C.

Step 7.

The powder coated seeds were placed in a conventional coating pan and rotation was commenced.

Step 8.

A coat of membrane solution (c) was applied to the powder coated seeds and the seeds so coated were allowed to dry. As in the case of Example 1 a coat of membrane solution (c) corresponds to 10 ml of solution (c) per 1,000 g of coated seeds.

Step 9.

One further coat of membrane solution (c) was applied to the coated seeds.

Step 10.

The finished pellets were allowed to dry at 45°–50° C.

The dried pellets were subjected to the dissolution test as described in Example 1 and Steps 7–10 were repeated until the desired dissolution rate at pH 7.5 was obtained.

EXAMPLE 3

Propranolol-containing pellets were prepared in the following manner.

(a) Powder Blend

Propranolol hydrochloride (#100 mesh) (1,000 g), talc (100 g) and fumaric acid (500 g) were blended in a standard pharmaceutical blender into a uniform powder.

(b) Polymer Solution

A solution of 19 parts (by volume) 20% polyvinylpyrrolidone (Kollidon K-30; Kollidon K-30 is a trademark) in isopropanol and 1 part (by volume) 33% Shellac (dewaxed) in ethanol was prepared.

(C) Membrane Solution

The membrane solution was prepared from the following ingredients.

1 part (by volume) 20% polyvinylpyrrolidone (Kollidon K-30) in isopropanol;

9 parts (by volume) 33% Shellac (dewaxed) in ethanol;

10 parts (by volume) isopropanol;

10 parts (by weight) talc;

Diethylphthalate (plasticizer), as required.

Pellet Making Procedure

Steps 1–4 were carried out as in Example 1.

Steps 2–4 were repeated until all of the powder (a) had been coated on.

Step 5.

The powder coated seeds were sealed with one application of polymer solution (b) and talc.

Step 6.

The powder coated seeds were oven dried at 45°–50° C. for at least 12 hours.

Step 7.

The powder coated seeds were placed in a conventional coating pan and rotation was commenced.

Step 8.

A coat of membrane solution (c) was applied to the powder coated seeds and the seeds so coated were allowed to dry. As in the case of Examples 1 and 2 above a coat of membrane solution (c) corresponds to 10 ml of solution (c) per 1,000 g of coated seeds.

Step 9.

Two further coats of membrane solution (c) were applied to the coated seeds.

Step 10.

The finished pellets were allowed to dry at 45°–50° C.

The dried pellets were then subjected to a dissolution test as described in Example 1 above. Steps 7–10 were repeated until a satisfactory dissolution rate was obtained. A total of 60 coats of membrane solution (c) was applied before the required dissolution rate was obtained. The dissolution rate of the product was as follows:

|          |       |
| -------- | ----- |
| 2 hours  | 9.9%  |
| 4 hours  | 21.9% |
| 6 hours  | 47.0% |
| 8 hours  | 79.0% |
| 10 hours | 95.3% |

Figure 1:
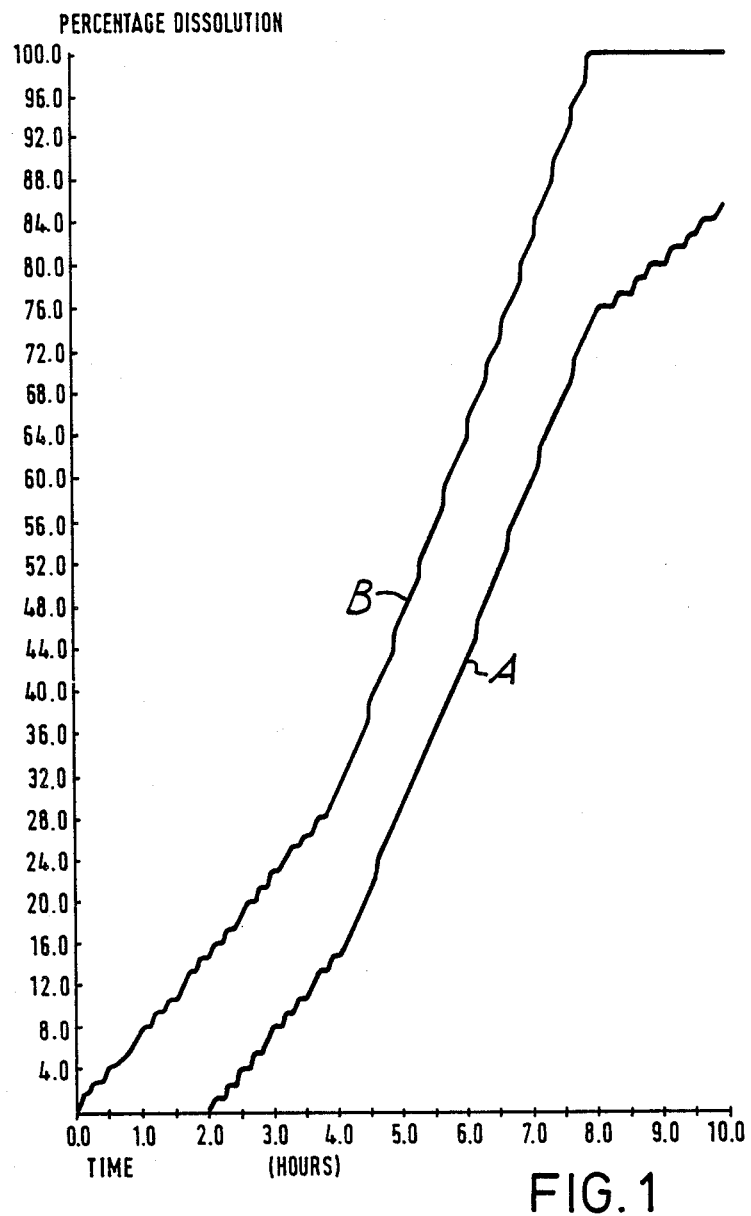
FIG. 1 is a graph of percentage dissolution versus time of pellets according to the invention. Curve B shows the maximum percentage dissolution per unit time and Curve A the minimum percentage dissolution per unit time permissible to achieve a peak plasma level between 8 and 10 hours.
Figure 2:
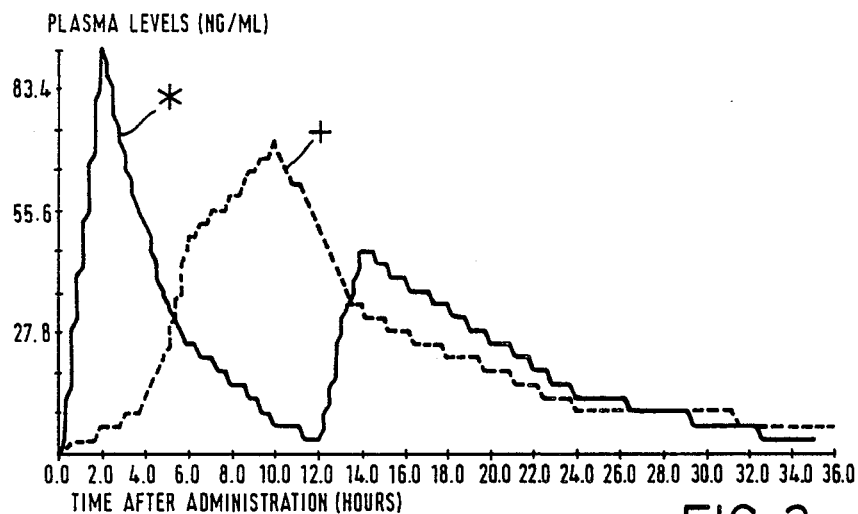
FIG. 2 is a graph of plasma levels (ng/ml) versus time after administration (hours) for a single dose of pellets prepared according to Example 3 in tablet form (160 mg) (+) compared with Inderal tablets (80 mg) (*) administered at 0 and 12 hours.

The graphs of FIG. 2 were drawn from the mean values obtained for six subjects according to the data listed in Tables 1 and 2.

As will be observed from FIG. 2 peak plasma levels occurred at 2 and 2.8 hours after the first and second Inderal dose, respectively. The propranolol prepared according to Example 3 (160 mg tablet) showed a peak plasma level at 8 hours.

Figure 3:
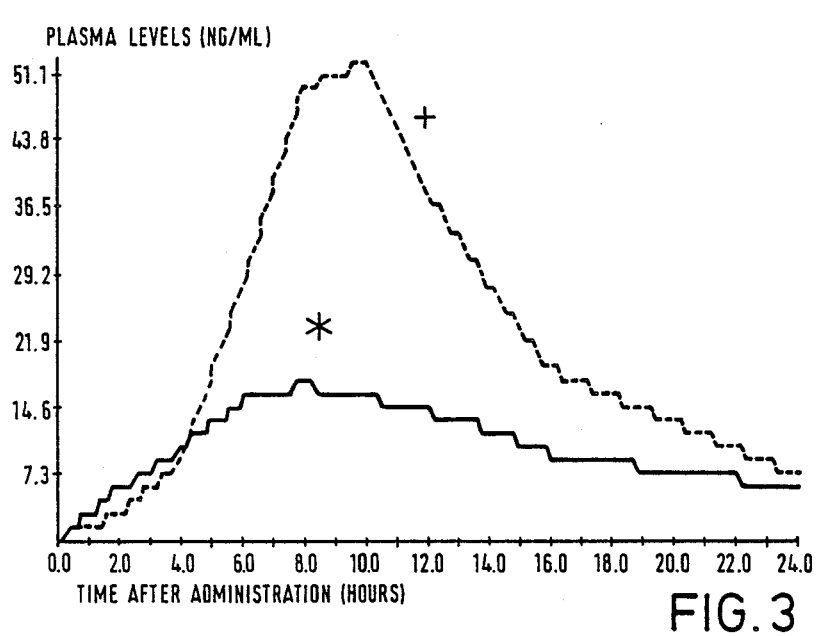

FIG. 3 is a graph of plasma levels (ng/ml) versus time after administration (hours) for a single dose of pellets prepared according to Example 3 in capsule form (120 mg) (+) compared with a single dose of Inderal LA capsules (160 mg) (*).

The graphs of FIG. 3 were drawn from the mean values obtained for six subjects according to the data listed in Tables 3 and 4.

As will be observed from FIG. 3 Inderal LA showed a peak plasma level at 9.3 hours and the propranolol prepared according to Example 3 (120 mg capsule) showed a peak plasma level at 8.7 hours.

TABLE 1

Inderal (80 mg b.i.d.)
Blood level study results - Summary of pharmacokinetic data

| SUBJ | HOURS AFTER ADMINISTRATION | | | | | | | | | | | | | | | AUC* |
|---|---|---|---|---|---|---|---|---|---|---|---|---|---|---|---|---|
| | 0.00 | 2.00 | 3.00 | 4.00 | 5.00 | 6.00 | 8.00 | 10.00 | 12.00 | 13.00 | 14.00 | 15.00 | 16.00 | 24.00 | 36.00 | |
| 1 | 0.00 | 147.30 | 133.90 | 101.43 | 65.20 | 50.16 | 42.60 | 19.99 | 11.73 | 58.00 | 103.06 | 60.62 | 64.33 | 29.10 | 2.28 | 1,555.34 |
| 2 | 0.00 | 122.19 | 79.45 | 63.40 | 54.99 | 33.98 | 22.26 | 10.23 | 5.51 | 32.95 | 55.22 | 49.87 | 37.39 | 15.60 | 3.49 | 988.57 |
| 3 | 0.00 | 39.40 | 26.15 | 18.74 | 15.75 | 8.95 | 3.78 | 4.87 | 0.00 | 0.00 | 4.46 | 23.16 | 27.93 | 3.64 | 0.00 | 340.17 |
| 4 | 0.00 | 103.88 | 64.74 | 48.11 | 23.34 | 15.01 | 7.23 | 0.00 | 0.00 | 55.05 | 60.48 | 51.30 | 32.69 | 3.78 | 0.00 | 680.72 |
| 5 | 0.00 | 69.83 | 55.43 | 42.36 | 28.36 | 24.73 | 14.98 | 0.00 | 0.00 | 12.87 | 34.94 | 40.98 | 37.60 | 8.74 | 0.00 | 643.33 |
| 6 | 0.00 | 73.40 | 41.40 | 33.84 | 15.96 | 16.82 | 9.70 | 8.70 | 4.07 | 0.00 | 23.39 | 33.92 | 35.95 | 18.11 | 0.00 | 669.62 |
| MEAN | 0.00 | 92.67 | 66.84 | 51.31 | 33.93 | 24.94 | 16.76 | 7.30 | 3.55 | 26.48 | 46.92 | 43.31 | 39.31 | 13.16 | 0.96 | 812.96 |
| ST DEV | 0.00 | 39.27 | 37.67 | 28.69 | 21.06 | 15.09 | 14.21 | 7.54 | 4.67 | 26.23 | 34.36 | 13.46 | 12.78 | 9.83 | 1.54 | 417.69 |
| **CV (%) | 0.00 | 42.38 | 56.35 | 55.90 | 62.07 | 60.49 | 84.82 | 103.28 | 131.36 | 99.05 | 73.23 | 31.08 | 32.52 | 74.64 | 159.95 | 51.38 |
| MAX | 0.00 | 147.30 | 133.90 | 101.43 | 65.20 | 50.16 | 42.60 | 19.99 | 11.73 | 58.00 | 103.06 | 60.62 | 64.33 | 29.10 | 3.49 | 1,555.34 |
| MIN | 0.00 | 39.40 | 26.15 | 18.74 | 15.75 | 8.95 | 3.78 | 0.00 | 0.00 | 0.00 | 4.46 | 23.16 | 27.93 | 3.64 | 0.00 | 340.17 |

*Area under the curve.
**Coefficient of variation.

TABLE 2

Controlled absorption propranolol prepared according to Example 3 (160 mg)
Blood level study results - Summary of pharmacokinetic data

| SUBJ | HOURS AFTER ADMINISTRATION | | | | | | | | | | | | | | | AUC* |
|---|---|---|---|---|---|---|---|---|---|---|---|---|---|---|---|---|
| | 0.00 | 2.00 | 3.00 | 4.00 | 5.00 | 6.00 | 8.00 | 10.00 | 12.00 | 13.00 | 14.00 | 15.00 | 16.00 | 24.00 | 36.00 | |
| 1 | 0.00 | 12.01 | 16.74 | 27.58 | 35.64 | 113.98 | 86.80 | 82.03 | 55.56 | 47.03 | 43.59 | 57.28 | 47.86 | 15.76 | 0.00 | 1,210.81 |
| 2 | 0.00 | 2.21 | 5.57 | 12.13 | 39.47 | 48.72 | 49.55 | 182.14 | 125.91 | 94.25 | 68.19 | 58.30 | 47.94 | 16.10 | 1.08 | 1,389.76 |
| 3 | 0.00 | 0.00 | 9.66 | 8.14 | 18.11 | 55.99 | 75.48 | 50.29 | 44.96 | 35.60 | 28.54 | 21.38 | 20.56 | 9.74 | 1.32 | 722.23 |
| 4 | 0.00 | 6.98 | 4.37 | 6.73 | 16.64 | 30.91 | 33.67 | 28.79 | 24.62 | 23.25 | 17.76 | 14.52 | 12.72 | 4.80 | 3.43 | 427.77 |
| 5 | 0.00 | 3.68 | 4.11 | 4.05 | 16.58 | 24.56 | 35.83 | 33.47 | 27.85 | 17.45 | 20.63 | 13.65 | 14.71 | 8.04 | 6.02 | 481.92 |
| 6 | 0.00 | 4.64 | 4.47 | 8.24 | 13.89 | 23.17 | 68.92 | 45.61 | 37.73 | 25.23 | 20.25 | 15.58 | 21.00 | 7.05 | 24.68 | 728.11 |
| MEAN | 0.00 | 4.92 | 7.49 | 11.15 | 23.39 | 49.55 | 58.37 | 70.39 | 52.77 | 40.47 | 33.16 | 30.12 | 27.46 | 10.25 | 6.09 | 826.77 |
| ST DEV | 0.00 | 4.19 | 4.98 | 8.47 | 11.12 | 34.24 | 21.95 | 57.85 | 37.57 | 28.35 | 19.59 | 21.61 | 16.15 | 4.68 | 9.36 | 390.70 |
| CV (%) | 0.00 | 85.11 | 66.58 | 75.96 | 47.56 | 69.09 | 37.60 | 82.19 | 71.20 | 70.05 | 59.07 | 71.74 | 58.82 | 45.70 | 153.66 | 47.26 |
| MAX | 0.00 | 12.01 | 16.74 | 27.58 | 39.47 | 113.98 | 86.80 | 182.14 | 125.91 | 94.25 | 68.19 | 58.30 | 47.94 | 16.10 | 24.68 | 1,389.76 |
| MIN | 0.00 | 0.00 | 4.11 | 4.05 | 13.89 | 23.17 | 33.67 | 28.79 | 24.62 | 17.45 | 17.76 | 13.65 | 12.72 | 4.80 | 0.00 | 427.77 |

*Area under the curve.
**Coefficient of variation.

TABLE 3

Inderal LA - 160 mg
Blood level study results - Summary of pharmacokinetic data

| SUBJ | HOURS AFTER ADMINISTRATION | | | | | | | | | | AUC* |
|---|---|---|---|---|---|---|---|---|---|---|---|
| | 0.00 | 2.00 | 4.00 | 6.00 | 8.00 | 10.00 | 12.00 | 14.00 | 16.00 | 24.00 | |
| 1 | 0.00 | 0.00 | 0.00 | 5.05 | 9.64 | 7.34 | 7.13 | 9.36 | 2.10 | 0.00 | 87.54 |
| 2 | 0.00 | 1.78 | 0.50 | 2.28 | 1.65 | 2.77 | 3.29 | 2.48 | 2.46 | 1.35 | 47.20 |
| 3 | 0.00 | 0.96 | 3.73 | 8.14 | 19.41 | 21.79 | 24.85 | 22.76 | 17.08 | 15.44 | 350.44 |
| 4 | 0.00 | 17.44 | 27.11 | 30.33 | 31.81 | 27.46 | 19.68 | 17.18 | 16.44 | 7.19 | 452.98 |
| 5 | 0.00 | 1.11 | 4.19 | 5.00 | 9.44 | 9.48 | 8.95 | 5.19 | 7.40 | 2.78 | 134.84 |
| 6 | 0.00 | 13.23 | 23.45 | 42.30 | 29.84 | 25.59 | 19.83 | 16.26 | 9.92 | 7.71 | 421.44 |
| MEAN | 0.00 | 5.75 | 9.83 | 15.52 | 16.97 | 15.74 | 13.96 | 12.21 | 9.23 | 5.75 | 249.08 |
| ST DEV | 0.00 | 7.56 | 12.14 | 16.65 | 12.14 | 10.48 | 8.62 | 7.80 | 6.54 | 5.67 | 179.69 |
| **CV (%) | 0.00 | 131.43 | 123.49 | 107.32 | 71.56 | 66.58 | 61.76 | 63.94 | 70.87 | 98.73 | 72.14 |
| MAX | 0.00 | 17.44 | 27.11 | 42.30 | 31.81 | 27.46 | 24.85 | 22.76 | 17.08 | 15.44 | 452.98 |
| MIN | 0.00 | 0.00 | 0.00 | 2.28 | 1.65 | 2.77 | 3.29 | 2.48 | 2.10 | 0.01 | 47.20 |

*Area under the curve.
**Coefficient of variation.

TABLE 4

Controlled absorption Propranolol prepared according to Example 3 (120 mg)
Blood level study results - Summary of pharmacokinetic data

| SUBJ | HOURS AFTER ADMINISTRATION | | | | | | | | | | AUC* |
|---|---|---|---|---|---|---|---|---|---|---|---|
| | 0.00 | 2.00 | 4.00 | 6.00 | 8.00 | 10.00 | 12.00 | 14.00 | 16.00 | 24.00 | |
| 1 | 0.00 | 0.00 | 6.43 | 20.31 | 69.20 | 68.80 | 45.67 | 34.97 | 10.72 | 1.47 | 550.24 |

TABLE 4-continued

Controlled absorption Propranolol prepared according to Example 3 (120 mg)
Blood level study results - Summary of pharmacokinetic data

| SUBJ | 0.00 | 2.00 | 4.00 | 6.00 | 8.00 | 10.00 | 12.00 | 14.00 | 16.00 | 24.00 | AUC* |
|---|---|---|---|---|---|---|---|---|---|---|---|
| 2 | 0.00 | 0.94 | 11.10 | 31.15 | 15.05 | 13.53 | 9.96 | 8.10 | 5.89 | 2.86 | 220.55 |
| 3 | 0.00 | 4.36 | 5.13 | 16.60 | 56.13 | 69.30 | 63.61 | 46.29 | 47.51 | 16.08 | 824.71 |
| 4 | 0.00 | 5.71 | 12.76 | 19.47 | 26.55 | 49.56 | 29.99 | 16.86 | 11.02 | 8.43 | 410.62 |
| 5 | 0.00 | 0.00 | 2.73 | 22.59 | 40.60 | 41.54 | 33.90 | 26.95 | 12.89 | 4.12 | 417.55 |
| 6 | 0.00 | 6.34 | 15.35 | 59.75 | 90.11 | 72.66 | 44.00 | 35.57 | 23.46 | 9.90 | 804.46 |
| MEAN | 0.00 | 2.89 | 8.92 | 28.31 | 49.61 | 52.56 | 37.86 | 28.12 | 18.58 | 7.14 | 538.02 |
| ST DEV | 0.00 | 2.92 | 4.89 | 16.18 | 27.83 | 22.81 | 17.99 | 13.87 | 15.32 | 5.46 | 238.69 |
| **CV (%) | 0.00 | 100.85 | 54.88 | 57.14 | 56.11 | 43.40 | 47.52 | 49.31 | 82.43 | 76.37 | 44.36 |
| MAX | 0.00 | 6.34 | 15.35 | 59.75 | 90.11 | 72.66 | 63.61 | 46.29 | 47.51 | 16.08 | 824.71 |
| MIN | 0.00 | 0.00 | 2.73 | 16.60 | 15.05 | 13.53 | 9.96 | 8.10 | 5.89 | 1.47 | 220.55 |

*Area under the curve.
**Coefficient of variation.

The blood level studies carried out and the results of which are given in Tables 1-4 showed that a 160 mg single dose of the propranolol prepared according to Example 3 had an equivalent plasma level AUC (area under the curve) (826.8 ng h/ml) as conventional Inderal tablets given at a dosage of 80 mg at 0 and 12 hours (813.0 ng h/ml). In contrast, a 120 mg single dose of the propranolol prepared according to Example 3 had a markedly higher plasma level AUC (538.0 ng h/ml) than a 160 mg single dose of Inderal LA (249.1 ng h/ml).

The propranolol of Example 3 showed a peak plasma level (85.0 ng/ml) intermediate the first and second Inderal peak values viz 92.7 ng/ml and 53.9 ng/ml respectively. In contrast, the propranolol of Example 3 (120 mg) had a markedly higher peak plasma level (58.5 ng/ml) than Inderal LA (160 mg) which had a peak plasma level of 20.2 ng/ml.

In terms of variability, the propranolol of Example 3 was similar to Inderal in:
(1) AUC variability

| Propranolol of Example 3 | % CV = 47.3 |
|---|---|
| Inderal | % CV = 51.4; |

(2) Variability over sample points

| Propranolol of Example 3 | % CV = 71.0 |
|---|---|
| Inderal | % CV = 76.2. |

However, the propranolol of Example 3 was far less variable than Inderal LA for parameters (1) and (2):
(1) AUC variability

| Propranolol of Example 3 | % CV = 44.4 |
|---|---|
| Inderal LA | % CV = 72.2 |

(2) Variability over sample points

| Propranolol of Example 3 | % CV = 63.1 |
|---|---|
| Inderal LA | % CV = 88.4 |

In terms of time-cover (length of time with a particular level of drug) over a range of plasma propranolol levels, the propranolol of Example 3 was equivalent to Inderal but even at a reduced dosage (120 mg) it was far superior to Inderal LA as shown in Table 5:

TABLE 5

| Propranolol Level (ng/ml) | Time Cover (h) | | | |
|---|---|---|---|---|
| | Propranolol of Ex. 3 (160 mg) | Inderal (80 mg × 2) | Propranolol of Ex. 3 (120 mg) | Inderal LA (160 mg) |
| 20.0 | 13.0 | 15.0 | 9.8 | 4.1 |
| 40.0 | 6.3 | 6.0 | 4.9 | 0.1 |
| 60.0 | 2.8 | 2.7 | 2.0 | 0 |

For two different drugs to be equally effective or for two different formulations of the same drug to be equally effective, not only must the intensity of the effect be the same (related to concentration) but also the duration of effect (related to duration of time cover at effective concentrations).

In order to demonstrate equivalence of two different formulations, therapeutic equivalence is presumed to follow from equivalence of plasma levels. The parameters regarded as important in defining plasma levels include AUC, Cmax (peak levels), Tmax (time of peak levels) and also "time coverage". In the case of a controlled or sustained release formulation this latter parameter is of particular importance because although the shape of the plasma level curve is deliberately altered it is important that the total length of time that a relevant plasma concentration is maintained should be similar for the sustained-release formulation and the standard product.

In the case of propranolol, a definitive "therapeutic" plasma concentration range has not yet been described. However, a comparison of timecoverage at plasma values in the range 20-40-60 ng/ml which cover the range of plasma levels observed following standard propranolol administration will allow a statement as to the equivalence or lack of equivalence of the products at levels that must include therapeutically important concentrations.

The data in Table 5 indicate the equivalence of the propranolol of Example 3 with conventional Inderal tablets and the much poorer performance of Inderal LA.

It will be appreciated from the foregoing description that the pellets according to the invention are more readily absorbed than conventional sustained release propranolol and that they exhibit excellent bioavailability.

What we claim is:
1. A controlled absorption propranolol containing pellet for oral administration, said pellet comprising:
 (A) a core of

(i) a powder mixture comprising propranolol or a pharmaceutically acceptable salt thereof and an organic acid selected from the group consisting of citric acid, tartaric acid, succinic acid, malic acid, ascorbic acid and fumaric acid or a mixture thereof, and (ii) a polymeric material comprising a major proportion of a pharmaceutically acceptable water-soluble polymer and a minor proportion of a pharmaceutically acceptable water-insoluble polymer, said core comprising layers of said powder mixture and said polymeric material superimposed one upon the other wherein said polymeric material is present in an amount sufficient to ensure that all of said powder mixture is coated into said core; and (B) a multi-layer membrane surrounding said core and containing a major proportion of a pharmaceutically acceptable film forming, water-insoluble polymer and a minor proportion of a pharmaceuticaly acceptable film forming, water-soluble polymer, the number of layers in said membrane and the ratio of said water-insoluble polymer to said water-soluble polymer being effective to permit release of said propranolol from said pellet at a rate allowing controlled absorption thereof over a twenty four hour period following oral administration, said rate being measured in vitro as a dissolution rate of said pellet in a buffer solution at pH 7.5 which, when measured in a basket assembly according to U.S. Pharmacopoeia XX at 37° C. and 75 r.p.m., substantially corresponds to the following dissolution pattern:

(a) from 0 to 15% of the total propranolol is released after 2 hours of measurement in said assembly;

(b) from 15 to 30% of the total propranolol is released after 4 hours of measurement in said assembly;

(c) from 43 to 63% of the total propranolol is released after 6 hours of measurement in said assembly;

(d) from 75 to 100% of the total propranolol is released after 8 hours of measurement in said assembly;

(e) from 85 to 100% of the total propranolol is released after 10 hours of measurement in said assembly.

2. A pellet according to claim 1, wherein the active ingredient of the core is propranolol hydrochloride.

3. A pellet according to claim 1, wherein the propranolol and organic acid are present in a ratio of 2:1.

4. A pellet according to claim 1, wherein the polymeric material of the core includes a major proportion of a pharmaceutically acceptable, water-soluble polymer selected from hydroxypropylmethycellulose and polyvinylpyrrolidone.

5. A pellet according to claim 4, wherein the polymeric material of the core includes a minor proportion, of a pharmaceutically acceptable, water-insoluble polymer selected from the group consisting of methylcellulose, ethylcellulose, propylcellulose and shellac.

6. A pellet according to claim 1, wherein the propranolol or pharmaceutically acceptable salt thereof, organic acid and polymeric material are built up on an inert core.

7. A pellet according to claim 6, wherein the inert core is a non-pareil seed having an average diameter in the range 0.3–0.7 mm.

8. A pellet according to claim 1, wherein the membrane includes a major proportion of pharmaceutically acceptable, water-insoluble polymer selected from the group consisting of methylcellulose, ethylcellulose, propylcellulose and shellac.

9. A pellet according to claim 8, wherein the membrane includes a minor proportion of a pharmaceutically acceptable, water-soluble polymer, the ratio of water-insoluble to water-soluble polymer being determined by the inherent solubility characteristics of the polymers selected.

10. A pellet according to claim 9, wherein the membrane consists of ethylcellulose and hydroxypropylmethylcellulose in a ratio of 9:1.

11. A pellet according to claim 9, wherein the membrane consists of a copolymer of acrylic and methacrylic acid esters which is slightly permeable to water and a copolymer of acrylic and methacrylic acid esters which is freely permeable to water in a ratio of 8:2.

12. A pellet according to claim 9, wherein the membrane consists of shellac and polyvinylpyrrolidone in a ratio of 9:1.

13. A capsule comprising pellets according to claim 1.

14. A tablet comprising pellets according to claim 1.

15. A pellet according to claim 1, wherein the polymeric material of the core comprises a major proportion of a copolymer of acrylic and methacrylic acid esters which is freely permeable to water and a minor proportion of a copolymer of acrylic and methacrylic acid esters which is slightly permeable to water.

16. A pellet according to claim 1, wherein the membrane consists of a copolymer of acrylic and methacrylic acid esters which is slightly permeable to water and a copolymer of acrylic and methacrylic acid esters which is freely permeable to water in a ratio of 8:2.

* * * * *